(12) United States Patent
Joyce et al.

(10) Patent No.: US 9,116,100 B2
(45) Date of Patent: Aug. 25, 2015

(54) METHOD FOR THE IDENTIFICATION OF MATERIALS IN A CONTAINER

(75) Inventors: David Edward Joyce, Bearpark (GB); Gary Gibson, Winning Durham (GB); Ian Radley, Bishop Auckland Durham (GB); Martin Senior, Wetherby (GB)

(73) Assignee: Kromek Limited, Sedgefield, Durham (GB)

( * ) Notice: Subject to any disclaimer, the term of this patent is extended or adjusted under 35 U.S.C. 154(b) by 851 days.

(21) Appl. No.: 13/265,504

(22) PCT Filed: May 24, 2010

(86) PCT No.: PCT/GB2010/050842
§ 371 (c)(1),
(2), (4) Date: Jan. 17, 2012

(87) PCT Pub. No.: WO2010/136790
PCT Pub. Date: Dec. 2, 2010

(65) Prior Publication Data
US 2012/0116691 A1    May 10, 2012

(30) Foreign Application Priority Data

May 26, 2009  (GB) .................................. 0908981.4
Sep. 4, 2009  (GB) .................................. 0915374.3

(51) Int. Cl.
*G01N 23/10*   (2006.01)
*G01N 23/087*  (2006.01)

(52) U.S. Cl.
CPC .............. *G01N 23/087* (2013.01); *G01N 23/10* (2013.01)

(58) Field of Classification Search
CPC ............................ G01N 23/087; G01N 23/10
USPC ........ 702/22, 27, 28, 30–32, 104; 378/5, 7, 8, 378/51, 53, 57, 62
See application file for complete search history.

(56) References Cited

U.S. PATENT DOCUMENTS 5,768,334 A    6/1998   Maitrejean et al.
8,699,662 B2 *  4/2014   Radley et al. ................... 378/53
(Continued)

FOREIGN PATENT DOCUMENTS

JP    2000215304 A    4/2000
JP    2001272357 A    10/2001
(Continued)

OTHER PUBLICATIONS

JP Office Action; Notice of Reasons for Rejection on JP Patent Appl. No. 2012-512455; 2 pages, Nov. 19, 2013.
(Continued)

*Primary Examiner* — Manuel L Barbee
(74) *Attorney, Agent, or Firm* — Drinker Biddle & Reath LLP

(57) ABSTRACT

Method for the identification of a homogeneous material (e.g. a liquid) in a container (e.g. a bottle) by measuring its X-ray or gamma spectrum and deriving its specific attenuation function. The method comprises building a database of the attenuation functions of empty containers, of containers filled with various fluid materials and of the contained fluid materials itself (by subtracting or devoluting the empty-container-attenuation-function from the filled-container-attenuation-function), recording the spectrum of an unknown material in a container and comparing this spectrum to the spectra in the database.

24 Claims, 5 Drawing Sheets

(56) References Cited

U.S. PATENT DOCUMENTS

| | | |
|---|---|---|
| 2009/0092220 A1 | 4/2009 | Chen et al. |
| 2011/0172972 A1* | 7/2011 | Gudmundson et al. ........... 703/1 |

FOREIGN PATENT DOCUMENTS

| | | |
|---|---|---|
| JP | 2004177299 A | 6/2004 |
| JP | 200591053 A | 4/2005 |
| JP | 2005265787 A | 9/2005 |
| JP | 2006118943 A | 5/2006 |
| JP | 2009109216 A | 5/2009 |
| WO | WO 2008/007976 | 1/2008 |
| WO | WO 2008/142446 A2 | 11/2008 |
| WO | WO 2009/024817 | 2/2009 |
| WO | WO 2009/024818 | 2/2009 |

OTHER PUBLICATIONS

International Search Report and the Written Opinion dated Sep. 23, 2010.

* cited by examiner

METHOD FOR THE IDENTIFICATION OF MATERIALS IN A CONTAINER

FIELD OF THE INVENTION

This invention relates to a method and apparatus for the identification and detection of contained materials such as liquids and the like, especially within containers.

The invention in particular relates to objects comprising containers of contained materials which by their nature will be expected to have a single generally homogeneous composition, for example fluid compositions such as liquids, including mixtures, solutions, emulsions, suspensions etc, like flowable compositions such as gels, pastes, creams, fine powders, and the like, aerosols etc. Where reference is made herein by example to contained liquids in objects such as liquid containers it should be appreciated that the invention is equally applicable to all such liquid, partly-liquid and other flowable materials having this essential mixed and generally homogeneous character when contained.

The invention particularly relates to an apparatus and method making use of high energy radiation such as x-rays or gamma-rays to scan objects where it is desirable to gain information about the internal contents and/or composition of the contained material. The invention may further relate to a method and apparatus that operates by or in conjunction with the generation of an image of the material, but is not limited to such imaging.

BACKGROUND

It is desirable to scan the contents of objects such as, for example bottles, at security and customs checkpoints to gain information about content based on radiation received at a detector after interaction with the object and obtain an indication that the contents of the object do not constitute a threat to security or a breach of customs regulations. It is also desirable to scan the contents of objects for other purposes such as quality control, content verification, degradation monitoring etc.

To ensure that the contents of an object are what they are claimed to be, it may be useful to scan the object and contents so that a high energy ionising radiation beam traverses a cross section of the object. It can be possible to obtain an indication of the materials composition from a numerical analysis of the resultant transmitted radiation beam intensity data and to compare the results of that analysis with a reference data set relating to materials of known composition.

The transmission of x-rays through a material can be given by the exponential attenuation law, as follows:

$$I/I_o = \exp[-(\mu/\rho)\rho t] \quad (1)$$

where
- $\mu/\rho$ = Mass attenuation coefficient. A material constant which is characteristic of the weighted elemental composition of a material;
- I = final intensity;
- $I_o$ = Initial intensity;
- $\rho$ = density of the material; and
- t = thickness of the material.

Thus by looking at the variation in the x-ray transmission as a function of changes in the thickness "t" of a material, for example, deductions can be made about the mass attenuation coefficient and the density of the material. These two parameters are characteristic of different materials and so materials identification becomes possible.

Instrumentation has been developed which is intended to non-invasively identify target liquids and like materials (that is, materials having similarly generally homogenous composition throughout) held within sealed containers. The target liquids or like materials may be liquids or like materials which pose a security threat if carried on-board an aircraft, liquids containing dissolved narcotics, or liquids requiring quality control, for example. According to techniques disclosed in our co-pending International Patent Application No. PCT/GB2008/050711 (Publication No. WO2009/024818), a container may be irradiated with a beam of x-rays and the transmission characteristics of the container and its liquid contents measured using an energy selective detector such as cadmium telluride or germanium.

The transmission characteristics of various contained materials held in a variety of containers could be recorded and held in a database. The database could then be used for comparison with in situ scanning of containers and contents to look for matched transmission characteristics and, therefore, target materials could be identified. One drawback of such a system would be that the database, to be effective, would be required to hold a very large amount of data relating to the transmission characteristics of a variety of liquids or like contents and a variety of containers. Interrogation of the database would be time consuming and, therefore, unsuitable for many intended uses, such as in airport security where time is often of the essence.

When the object being scanned is a contained material which by its nature will be expected to have a single generally homogeneous composition, for example being a fluid composition such as a liquid as above described in a container, both the contained material and the container itself are subject to individual component variables, such as: the type of contained material, the composition or concentration of a contained material, the path length of high energy ionising radiation in the contained material, the material from which the container is made, and the thickness of the wall of the container, for example.

In order to provide a faster and accurate matching of data from a numerical analysis of resultant transmitted radiation beam intensity data from a scan of a container and its contents, it would be desirable to remove the component of the data relating to the container itself, thereby resulting in data relating to the contents only which may then be compared with a reference data set relating to content materials of known composition.

There is a need for an improved analytical tool for non-invasively identifying a contained material such as a liquid within a container.

Furthermore, there is a need for an improved method, system and apparatus for undertaking scanning of objects and their contents using high energy ionising radiation, where the identification and analysis of the contents is made without interference from the object itself.

SUMMARY OF THE INVENTION

In accordance with the invention in a first aspect a method of obtaining radiation data useful for the identification and detection of composition of a contained material such as a liquid comprising the steps of:

a) providing a radiation source and a radiation detector system spaced therefrom to define a scanning zone therebetween; the detector system being capable of detecting and collecting spectroscopically resolvable information about incident radiation;

b) collecting intensity information about radiation incident at the detector system, and hence interaction of a container of known material composition and of known wall thickness, absent any contents, in the scanning zone with incident radiation from radiation received at the detector system after interaction with and for example after transmission through the container;

c) repeating step b) for a plurality of different containers, each of known material composition and known wall thickness, and being absent any contents; to obtain a data set of intensity information relating to containers of known material compositions and known path length through the container;

d) evaluating a numerical relationship relating to the plurality of containers to generate a first analytical function which describes spectroscopically resolvable intensity information about radiation incident at the detector system after interaction with a container of known material composition relative to the path length through the container;

e) repeating steps b) to c) with the same containers now containing a material such as a liquid of known composition to obtain a data set of intensity information relating to container and contents of known material compositions and known path length through the container and contents;

f) deconvolving the data generated at step e) from equivalent data generated for an empty container, for example generated at steps b) to c), to obtain a data set of intensity information relating contained material of known material composition to known path length through the liquid;

g) evaluating a numerical relationship relating to the known contained material to generate a second analytical function which describes spectroscopically resolvable intensity information about radiation incident at the detector system after interaction with a contained material such as a liquid of known composition relative to the path length through the contained material.

Thus, in accordance with the invention, empty container intensity data is collected and used to generate a first analytical function for the interaction of the radiation with the container wall, for example comprising a line equation giving a thickness modified signature for attenuation by the wall. The first analytical function is generated for containers of a known composition and plural known wall thicknesses. Wall thicknesses may be measured for example normal to the surface, or in another appropriate direction, for example corresponding to a beam path direction.

The important point is that data is generated relating intensity to path length through the container for a range of path lengths for one or more known material compositions of container, the path length being a function of wall thickness and beam direction. This data is then used to generate a first analytical function which relates intensity to path length through the container for a given container composition.

This analytical function may be used in the various ways set out below, for example instead of measured data for similar containers, for example to populate a dataset with virtual bottle data.

More preferably, steps b) to d) may be repeated for containers of varied wall thicknesses having plural compositions. Thus, plural first analytical functions may be generated for plural container compositions.

These data or functions may be used to generate further analytical functions relating intensity to composition, particularly in the case where composition is known to vary continuously across a range (for example where a mutlicomponent container material has a range of component proportions). Such additional analytical functions may confer further utility without departing from the principles of the invention.

Further intensity data with the same containers now containing a generally homogenous material such as a liquid of known composition is collected and used to generate a dataset of intensity information representative of the result of interaction of the radiation with the container wall and contents. Reference may be made herein to such containers as filled containers. It will be understood that this is merely to distinguish from empty containers. No implication is made that such containers are filled to capacity, merely that the containers now contain a liquid or like material.

The data thus provides, for containers and contents of known material composition, data relating intensity to known path length through the combination of container and contents. Again, it is deriving a relationship to effective path length that is the key, path length being derivable for example from known container wall thickness and internal dimension with known beam direction.

A dataset of notional free contents data may then be generated by deconvolving the data generated at the step of measuring filled containers from suitable data generated for an empty container. The result is a data set of intensity information relating contents of known material composition to known path length through the contents alone, notionally free of container.

Empty container data is subtracted from filled container data (where subtracted is understood in the general sense as removal of the attenuation effect of the container, and not in the narrow sense as implying any particular arithmetical relationship between the first and second sets of data). Empty container data may be measured specifically for this purpose. Data may be taken from that recorded at the steps of measuring empty containers set out above. The first analytical function may be used to generate empty container data virtually, which is then subtracted from the filled container data. In all such cases, the result is a dataset of data items each representing a virtual container-free sample of contained material.

This deconvolved data is used to generate a second analytical function which describes spectroscopically resolvable intensity information about radiation incident at the detector system after interaction with a contained material of known composition relative to the path length through the contained material alone, with the container virtually removed. The data is thus used to generate a first analytical function which relates intensity to path length through the contents only for a given contents composition. The second analytical function for the interaction of the radiation with the contents for example comprises a line equation giving a path-length modified signature for attenuation by the contained material with the container virtually removed.

This analytical function may be used in the various ways set out below, for example instead of measured data for contents in other intermediate configurations of containers, for example to populate a dataset with virtual contents data.

More preferably, the method may be repeated for contents having plural compositions. Thus, plural second analytical functions may be generated for plural contents compositions. These may be used to generate further analytical functions relating intensity to composition, particularly in the case where composition is known to vary continuously across a range (for example where a contained material is a liquid mixture having a range of component proportions, where it is a solution is of varying strength etc). Such additional analytical functions may confer further utility to the product of the method.

However, at its most basic, the product of the method of the invention is a first analytical function relating intensity to path length through a container wall (and more preferably plural such functions for plural materials) and a second analytical function relating intensity to path length through "free" contents and more preferably plural such functions for plural contents).

These functions may be used in various as a means of saving effort when processing contained liquids or like materials in the future and for example matching measured to predicted data for identification purposes, including without limitation the generation of additional data for intermediate cases, the population of reference databases of virtual containers/contents etc.

Empty container data may simply be subtracted from filled container data on a data item by data item basis to generate a set of data items each representing a virtual container-free liquid or other contained material sample.

In an alternative case, filled container data may be used to generate a third analytical function which describes spectroscopically resolvable intensity information about radiation incident at the detector system after interaction with a container of known material composition and known thickness normal to the surface of the material of the container, containing a contained material such as a liquid of known composition. This third analytical function may be used to generate deconvolved data, and for example to generate the second analytical function in a deconvolving step of subtracting the first analytical function from the third analytical function to provide a second analytical function which describes spectroscopically resolvable intensity information about radiation incident at the detector system after interaction with a contained material such as a liquid of known composition as it passes through the scanning zone.

The first analytical function is deconvolved from the third to generate the second analytical function for the interaction of the radiation with the "free" contents, for example comprising a line equation giving a thickness modified signature for attenuation by the contained material such as the contained liquid. That is to say, the contribution attributable to the wall as provided for in the first analytical function is deconvolved or subtracted from the contribution attributable to the combination provided for in the second analytical function (where subtracted is understood in the general sense as removal of the attenuation effect from the deconvolved function, and not in the narrow sense as implying any particular arithmetical relationship between the first and second analytical functions) to produce a third analytical function relating the interaction of the radiation with the contents.

The contained material comprises a material which by its nature will be expected to have a single generally homogeneous composition on a macroscopic scale, and thus a response to the source which is generally dependent essentially only on path length through the contained material. Example contained materials might be fluid compositions such as liquids, including mixtures, solutions, emulsions, suspensions etc, like flowable compositions such as gels, pastes, creams, fine powders, and the like, aerosols etc.

The detector system is capable of detecting and collecting spectroscopically resolvable information about incident radiation in the sense that it is adapted to differentiate incident radiation simultaneously into a plurality of differentiated energy bands across the spectrum of the source. For example, the detector system exhibits a spectroscopically variable response across at least a part of the source spectrum allowing such simultaneous differentiation of incident radiation into a plurality of energy bands. An analytical function describes spectroscopically resolved intensity information about radiation incident at the detector system based upon such differentiation.

Preferably at least the second and more preferably at least the first and second of the analytical functions are so developed as to describe intensity information about radiation incident at the detector system across the spectrum of the radiation source for multiple permutations of different path lengths.

For example, a further step may comprise the step of:
generating a fourth analytical function which describes intensity information about radiation incident at the detector system after interaction with a container of known composition as it passes through the scanning zone across the full spectrum of the radiation source for all permutations of different container path lengths; and/or the step of:
generating a fifth analytical function which describes intensity information about radiation incident at the detector system after interaction with a liquid of known composition as it passes through the scanning zone across the full spectrum of the radiation source for all permutations of different path lengths through the contained material.

The process is repeated across a range of containers and contained materials such as liquids likely to be encountered. In this way, a library of analytical functions may be derived and/or a library of data may be provided of intensity information for liquids of known composition. Such a library of data may be populated by measured data items, virtual data items generated via the analytical function, or a combination of the two. The library of data provides reference information for a contained materi, without the container characteristics, thereby providing an accurate and rapid matching process for target liquids. In this way, a scanned liquid or like contained material can be matched against the database of characteristics of target contained materials without interference from the container characteristics. A library of data may be provided of intensity information for bottles of known composition. Such a library of data provides reference information for a bottle without the liquid or other contained material characteristics. Additionally or alternatively to its use to populate a library of data for such a reference comparison, an analytical function may be used as a direct numerical processing tool for measured intensity data.

An analytical function relating intensity information about radiation incident at the detector system after interaction with a container and an analytical function relating deconvolved intensity information about radiation incident at the detector system after interaction with a liquid, comprising as above defined the first and second analytical functions, or as the case may be the fourth and fifth analytical functions, and for example being thickness modified signatures for wall and liquid or like contents respectively, may be combined to produce an output which describes intensity information about radiation incident at the detector system after interaction with a contained material of known composition as it passes through the scanning zone across the spectrum of the radiation source for multiple permutations of different path lengths.

For example, in a preferred embodiment of the method, representing an enabling practical solution to minimize the computational overhead of running calculations during inspection, a container analytical function and a contents analytical function such as a liquid analytical function may be combined to populate a database with a range of virtual filled bottles of multiple permutations of different radiation path lengths.

In this way, a library of data is provided of intensity information for contained liquids or other like materials of known composition in known containers. The database provides reference information for a full range of likely contents/container combinations, thereby providing an accurate and rapid matching process for target contents. In this way, a scanned container can be matched against the database of characteristics and a target contained material such as a target contained liquid indentified.

Thus, in the preferred case, the method is a method of generating a library of data of intensity information for expected scenarios, for example comprising a library of data of intensity information for liquids or other like materials in isolation and/or for contained liquids or other like materials of known composition in known containers.

In a further aspect of the invention a method for the identification and detection of composition of a contained material such as a contained liquid comprises:
the performance of the steps above described to generate the said analytical functions, and in the preferred case to generate a library of data of intensity information for contained materials such as liquids in isolation and/or for contained materials such as liquids of known composition in known containers; collecting intensity information about radiation incident at the detector system, and hence interaction of, an unidentified contained material, from radiation received at the detector system after interaction with and for example after transmission through the unidentified contained material; using the analytical functions, for example by comparing measured intensity data for the unidentified contained material with the said library of data of intensity information, to identify the contained material.

In a preferred embodiment, a thickness filter may be applied which rejects any potential database matches outside a practical/measured bottle thickness range.

Thus, in accordance with the general principles of the invention, an object under test is scanned by subjecting it to a source of incident high energy radiation, and by detecting radiation at a detector system after interaction with the object and its contents, and in a particular preferred case at least by detecting radiation transmitted through the object and its contents. As will be familiar, the attenuation of radiation as it is transmitted through an object can give useful information both about the structure of the object and about its composition and thus in the present case about the structure of the object and the composition of its contents. The method thus conveniently comprises determining the attenuation of incident radiation by an object in the scanning zone during each scanning step.

The invention in particular comprises the collection and analysis of radiation after transmission through an object and contents under test. The invention in particular comprises a determination of the attenuation of that radiation relative to initial incident intensity. It is well known that the attenuation of transmitted radiation by a material is a specific material property which can be characteristically linked to and functionally related to certain physical parameters of the source radiation, such as incident intensity, incident energy etc.

The technique is intrinsically a comparative one since it involves looking for changes in a signature after it has passed through a test object. The invention is not limited by comparator. For example the skilled person may choose to use as the comparator an I0 measurement, a reference/calibration standard or even a virtual standard resulting from careful and reproducible configuration of the system.

For example, incident intensity is measured via a calibration step in which the system is operated without an object in the scanning zone and intensity information about radiation incident at the detector system is used to generate an incident intensity dataset for the above analysis.

In preferred possible embodiment of the method, intensity data comprising at least the intensity information collected during a scanning step is numerically analysed against a suitable functional relationship relating transmitted to incident intensity and the results compared with a library of suitable data with the objective of providing an indication of material content. For example, a ratio is determined of incident and transmitted intensity, and this ratio is used to determine a coefficient of mass attenuation, which can then be related to a library of equivalent coefficient data for expected target or component materials to gain information about the likely composition of the object and contents under scan. However, it is an advantage of the method, particularly in the preferred case where a database is generated of contained material or virtual bottle signatures, that such a numerical analysis may be unnecessary, and that identification is instead made by a comparison of the measured transmission data with such a database.

The object being scanned can be positioned for movement in the vertical or horizontal plane depending on the application. For security or customs screening of liquids in bottles it is envisaged that the bottle will be mounted in a holder and moved through a generally vertical plane as mounting the bottle horizontally could result in spillage of threat materials. Mounting an object such as a bottle for vertical movement would require some sort of fastening to keep the object in place during the scanning movement so the object is preferably mounted at an angle of between 1° and 80° from vertical, preferably at an angle of between 5° and 45° and more preferably between 5° and 30°.

Many objects, such as containers, and for example bottles or cartons of liquids, have a regular shape defining a through thickness direction through which they might usually be scanned. For example such a thickness might be defined by the parallel sides of an object, or by diametrically opposite points on the surface of an object. The radiation beam can be arranged so that it is incident perpendicular to the surface of such an object. That is to say, it passes through an object normally to its surface and in such a through thickness direction. If the radiation beam is arranged to pass through the object at an angle other than perpendicular then the beam passes through an increased thickness of the object contents which can improve beam absorption and hence analysis of the object contents. For example, the radiation beam is preferably arranged to pass through an object at an angle of between 0° and 80° away from normal to the surface, preferably between 5° and 45° and more preferably between 5° and 30°. If the object is mounted at an angle of between 1° and 80°, preferably between 5° and 45° and more preferably between 5° and 30° such as is described above, then using a generally horizontal beam arrangement will give the desired increase in beam path length through the object contents.

The radiation source preferably comprises a source to deliver high-energy radiation such as ionising radiation, for example high-energy electromagnetic radiation such as x-rays and/or gamma rays, and the detection system is adapted correspondingly to detect radiation in this spectrum. The radiation source for example is a broadband source such as a broadband x-ray or gamma-ray source capable of producing broad spectrum emission over a wide range of energies. The detector system preferably exhibits a spectroscopically variable response across at least a part of the source spectrum allowing spectroscopic information to be retrieved and allowing intensity information to be detected at a plurality of differentiated energy bands across the spectrum of the source.

For each "scanning event" (that is, for a measurement of intensity via a given radiation path incident upon and for example passing through the object/object and contents in a given position) an "intensity dataset" is collected representing the collected intensity incident at the detector system across at least part of a source energy spectrum. Preferably, in accordance with the method of the invention, each such intensity dataset is resolved across at least two and more preferably at least three separate energy bands across the spectrum of the source. An intensity dataset thus constitutes a dataset of intensity information related to frequency/energy which is resolvable into such a plurality of bands to produce a corresponding plurality of transmitted intensity data measurements relating to a given scanning event and hence a given transmission path through the object and contents under test.

In one possible embodiment, a single broad spectrum source may be used. In this embodiment the method of the invention may involve using a broad spectrum detector or detector array and/or a single narrow spectrum detector to detect incident radiation monochromatically. Alternatively incident radiation may be resolved spectroscopically with a single broad spectrum source incident upon a detector or detector array adapted to resolve information across the spectrum of source using the inherent properties of the detector and/or incident upon multiple detector arrays with narrow band responses. In the preferred case, incident radiation is resolved spectroscopically across at least three and more preferably at least five energy bands within the source spectrum. This can produce data susceptible of more powerful manipulation than monochromatic data. Thus, in this preferred case, the detector system is adapted to generate spectroscopic information about incident and especially transmitted radiation at least to the extent of resolving at least three and preferably at least five energy bands. Preferably, the detector exhibits a spectroscopically variable response across at least a substantial part of the spectrum of the radiation source allowing detailed spectroscopic information to be retrieved.

Similarly the source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

The source is preferably capable of generating a sufficiently broad spectrum of radiation to enable the spectral resolution necessary for the performance of the invention. Preferably the source generates radiation across at least one or more parts of the range of 20 keV to 1 MeV, and more preferably across at least a part, and for example a major part, of the range of 20 keV to 160 keV. For example the source generates radiation ranging across at least one bandwidth of at least 20 keV within the given range. For example the spectrum is such that at least three 10 keV bands can be resolved within that range.

It is preferable that the detector system is enabled to detect radiation in a manner which is spectroscopically resolvable by the data processing apparatus. Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the source spectrum. For example, the detector system or element comprises a semiconductor material or materials preferably formed as a bulk crystal, and for example as a bulk single crystal (where bulk crystal in this context indicates a thickness of at least 500 µm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_bTe$ where $a+b<1$ and a and/or b may be zero.

Combination of these and any other such materials may be considered which give spectroscopic detection rather than merely detecting amplitude of radiation after interaction with object and contents.

Preferably, a beam of a particular geometry, such as a pencil beam geometry or a fan or curtain beam, is used aligned perpendicular to direction of movement of the object.

In a preferred embodiment a simple pencil beam may be provided in conjunction with a simple single pixel detector or linear array detector. Alternatively, a beam may be collimated to have a spread in at least one dimension, for example in conjunction with one or more linear detectors. Only one pixel is needed for the detector if a pencil beam geometry is used. A linear array or area array used with a pencil beam can provide the capability to detect additional information such a scatter radiation. If a fan beam geometry is used a linear detector is preferred arranged perpendicular to the direction of movement of the object and within the area of the beam. Conveniently, a linear detector may comprise a linear array of a plurality of individual detector elements.

The radiation source is adapted to emit such a beam. A collimator is preferably provided between the source and the object under test, for example in the vicinity of the source, to produce an emitted beam of suitable geometry from the source. In particular, the source beam is collimated to produce a pencil beam.

Additionally or alternatively, the beam may be collimated after interaction with object and contents under test, for example in the vicinity of the detector, to allow transmitted radiation to pass to the detector but for example to restrict any scatter radiation from reaching the detector.

At its simplest, the invention may simply comprise a method for extracting from intensity data, at single or multiple spectral bands, an indication of material composition in the transmission path, for example by calculating a mass attenuation coefficient for an object in the transmission path and making a suitable library comparison. It need not generate an image.

However, it is not excluded that the invention may form part of a scanning imaging system. In accordance with this possible embodiment, the dataset of information about radiation incident at the detector, or at a further, imaging detector, especially information collected during the first, object scan, is used to generate an image of an object in the scanning zone.

Preferably the method comprises collecting data regarding the intensity of transmitted radiation after interaction with an object in the scanning zone and the data regarding the intensity of transmitted radiation is processed at the detector both numerically as above described and to produce one or more images and for example a succession of images as an object moves through the scanning zone.

For clarification it should be understood that where used herein a reference to the generation of image is a reference to the creation of an information dataset, for example in the form of a suitable stored and manipulatable data file, from which a visual representation of the underlying structure of the object under investigation could be produced, and references to displaying this image are references to presenting an image generated from such a dataset in a visually accessible form, for example on a suitable display means.

The method of the invention conveniently further provides the additional step of displaying such generated image or images, and in the case of multiple images might involve displaying such images simultaneously or sequentially.

Each collected image may be resolved spectroscopically across a plurality of bands each intended to generate an image across a part of the overall spectrum, so that the bands together allow the generation of an energy-differentiated composite image or succession of images.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
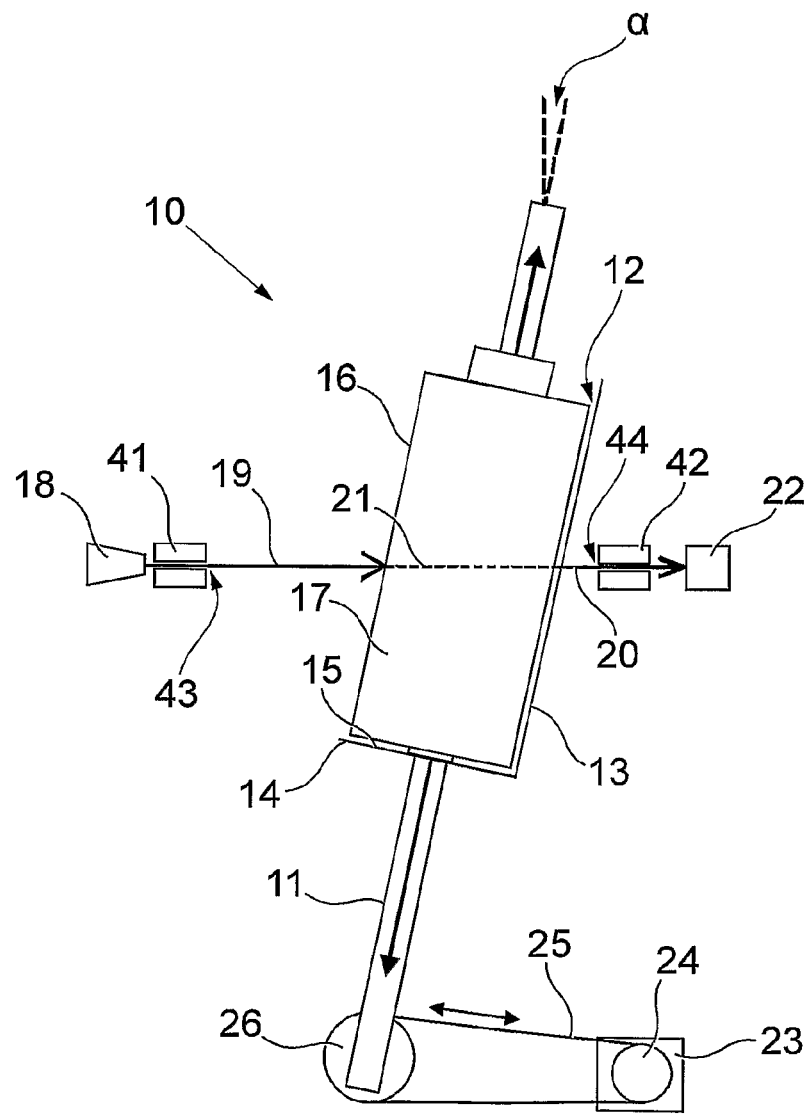
FIG. 1 is a schematic representation of an apparatus of the invention.

In the apparatus of the invention illustrated in FIG. 1 an embodiment of a possible apparatus to implement the invention is shown comprising a bottle scanner for scanning liquids in bottles and like objects using x-ray radiation. Although reference is made herein by example to contained liquids it will be appreciated that the invention is similarly applicable to all compositions materials having this essential mixed and generally at least macroscopically homogeneous character when contained such as liquid mixtures, solutions, emulsions, suspensions etc, like flowable compositions such as gels, pastes, creams, fine powders, and the like, aerosols etc.

The bottle scanner 10 is provided with a linear slider shaft 11 to move a bottle holder 12 that is fixedly connected to the linear slider shaft 11 for movement therewith. The linear slider shaft 11 is capable of moving the bottle holder 12 in two directions.

The bottle holder 12 comprises a back member 13 against which the bottle 16 rests and a base member 14 with a top surface 15 onto which the bottle 16 sits. The bottle 16 is nested against and into the bottle holder 12 by virtue of the holder and linear slider shaft being inclined at an angle α. In the example this might be an angle of 15° from vertical. For a bottle, an angle of between 5° and 30° might be convenient. Other shapes of objects or containers might be held at different optimum angles.

The bottle holder back member 13 is preferably provided with an opening (not shown) to allow a clear path for the x-ray beam to pass from the bottle to the detector. The opening in the back member 13 could be a slot shaped aperture running from the top to the bottom of the back member. The slot aperture could be a narrow slot that provides some beam collimation with a width sufficient to allow the beam to pass through unimpeded but narrow enough to restrict any scatter radiation from reaching the detector 22. Additional or other alternative collimation of the beam on the transmission side could be provided.

The movement of the bottle holder 12 and bottle 16 along the linear slider shaft 11 is caused by the rotation of the electrically powered stepper motor 23. The motor causes the pulley 24 to rotate, which drives belt 25 which, in turn, drives the rotation of pulley 26. The rotational motion of pulley 26 is converted into a rotation of a suitable drive such as a screw drive (not shown) in the linear slider shaft 11 which creates the linear motion of the bottle holder 12.

The motor is capable of rotation in either direction and by controlling the direction of rotation of the motor the direction of movement of the bottle holder 12 and bottle 16 can be determined.

As the bottle is moved along the direction of the linear slider shaft it is caused to pass through an x-ray beam 19. The incident beam 19 is generated by a source 18, preferably a tungsten source so that it has a broad spectrum of energies present in the beam.

The x-ray beam 19 is aligned horizontally. As the bottle is inclined at an angle α from the vertical the beam does not strike the bottle perpendicular to the bottle's surface. This preferred arrangement gives an increased absorption path for the beam as it passes through the bottle and its contents.

The incident beam 19 passes through the bottle 16 and bottle contents 17 where absorption and scatter will take place along beam path 21 before the transmission beam 22 emerges from the bottle and is detected by detector 20.

The x-ray beam is preferably collimated by primary collimator 41 provided with aperture 43 and positioned close to the source 18 and is preferably a pencil beam with one dimensional geometry.

The transmission x-ray beam 20 is preferably collimated through an appropriate aperture 44 in secondary collimator 42 before it arrives at detector 22.

The detector 22 is preferably a single pixel aligned with the collimated x-ray beam. The detector generates a signal representative of the intensity and energy of interactions with photons from the transmission x-ray beam 20. These signals are then processed as detailed in FIG. 2 below. In the embodiment the detector comprises material capable of spectroscopic resolution of incident x-rays, and in the specific example comprises cadmium telluride (CdTe) although it will be appreciated that alternative materials could be used.

Additional analysis capability could be provided by the use of additional detectors to detect those parts of the x-ray beam that have been scattered in the forward and/or backwards directions. The transmission beam 20 and forward scattered x-ray beams could be detected by the use of linear or area arrays.

Figure 2:
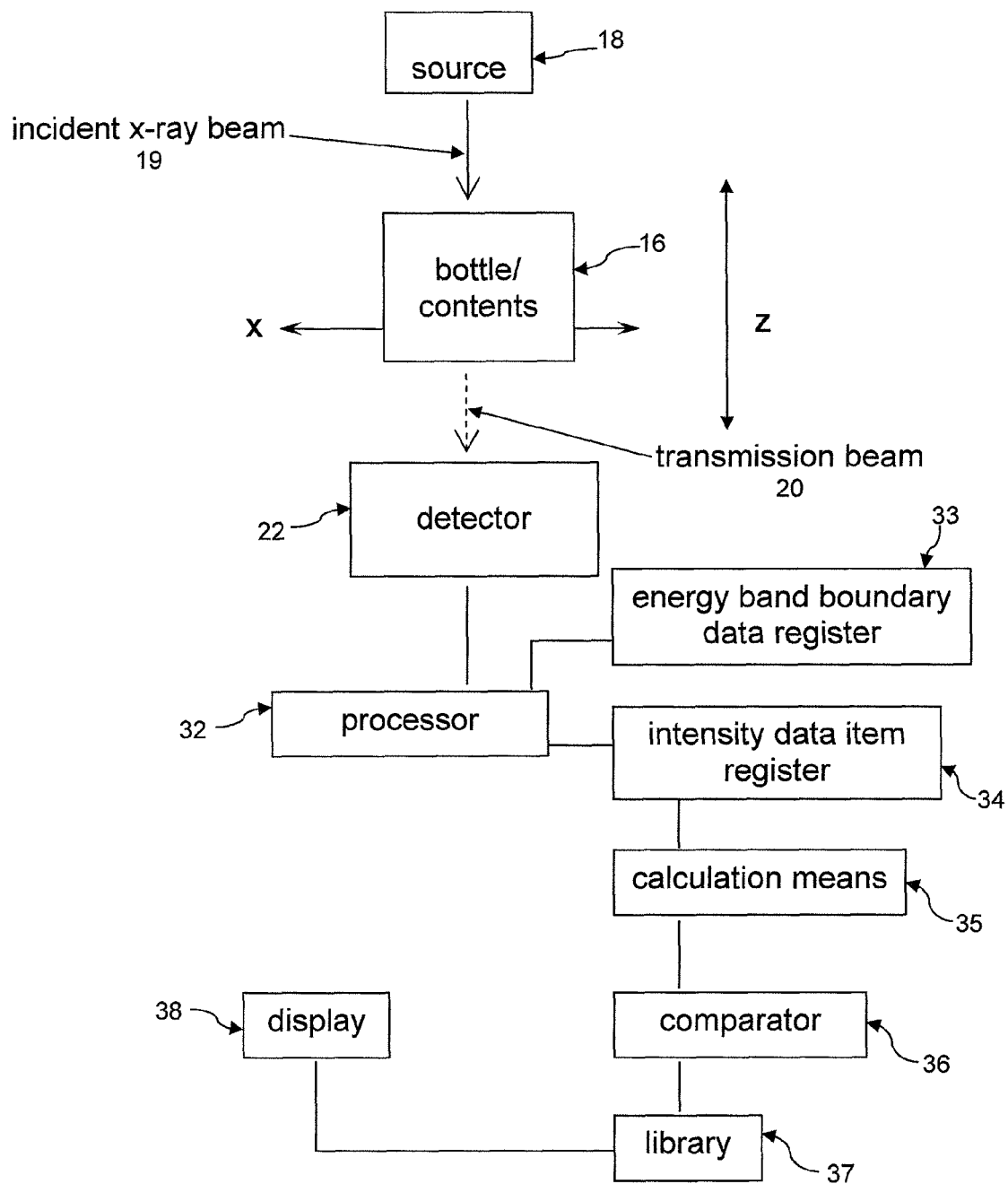
FIG. 2 is general schematic of a possible apparatus to implement the invention including an apparatus of FIG. 1.

In the general schematic representation of FIG. 2, a single ray path only is shown for simplicity. An x-ray source 18 and laterally spaced detector apparatus assembly 22 together define a scanning zone Z between them. In use, a bottle to be scanned is brought into an x-ray beam path by being placed in a bottle holder such as that shown in FIG. 1 and being moved in direction X through the scanning zone by a mechanism such as that described in FIG. 1 such that the x-ray beam passes through the bottle along its axis.

In the illustrated example, a bottle sits in the scanning zone Z. An incident beam 19 from the x-ray source is illustrated. In this simple schematic, the incident beam is represented by the line 19. The transmitted beam 20 is incident upon a single detector 22.

The detector 22 is in data communication with a processor 32. The inherent spectral resolution of the material in the detector allows the processor 32 to resolve this image differentially across a plurality of pre-set frequency/energy bands in accordance with the principles of the invention by reference to energy band boundaries stored in the data register 33.

In the example embodiment a tungsten x-ray source, is used. A typical spectrum such as might be generated by tungsten of initial intensity against wavelength is illustrated in FIG. 3.

The main purpose of FIG. 3 is to illustrate two possible ways in which the spectrum may be resolved in accordance with a possible embodiment. In each case, the spectrum is shown resolved across five frequency bands.

Figure 3A:
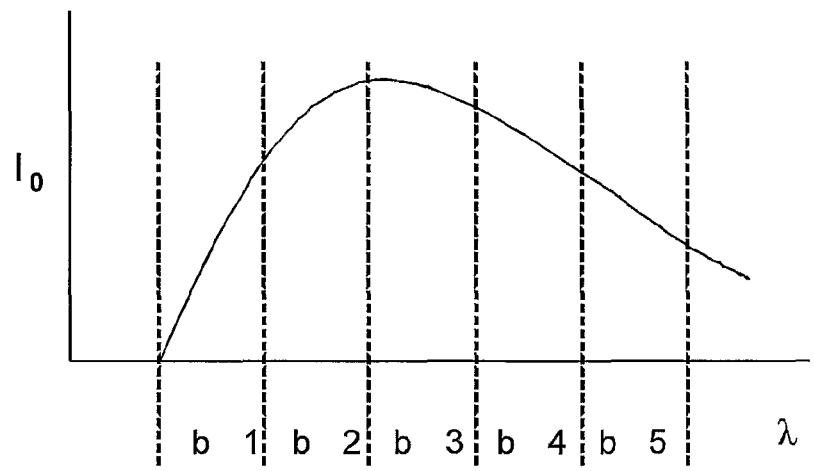
FIG. 3 illustrates a typical radiation source spectrum, and illustrates how it is partitioned to implement the invention in conjunction with an imaging operation.
Figure 3B:
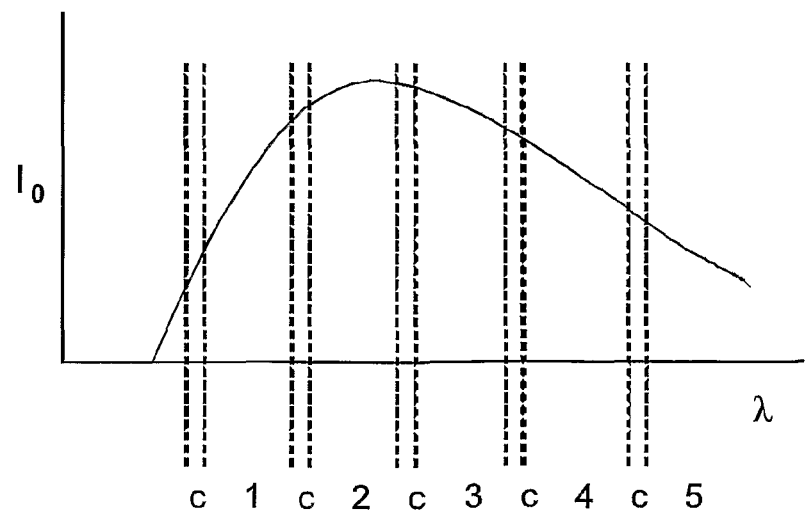

The schematic illustrates two ways in which the spectrum may be resolved. In FIG. 3a, the bulk of the generated spectrum is divided between five relatively broad energy bands $b1$ to $b5$. In FIG. 3b, five relatively narrow bands, which may approximate even to individual energies, are defined $c1$ to $c5$. Neither alternative is in contradiction with the principles of the invention, and any combination may be used to generate useful results either for the numerical analysis of the invention or, in a preferred embodiment, for spectroscopically resolved imaging to give further information about an object and contents under investigation.

In an example embodiment, the same principles may be used to generate general representative functions for a range of bottles and contents, and for example to populate a database of virtual bottles and contents, and to characterise and identify the material contents of an unknown bottle under investigation. In the example embodiment, the data is analysed numerically. The processor 32 further acts in relation to a series of identified frequency bands, for example those in FIG. 3a or 3b, and in this function uses the data to generate a representative quantification of, and for example an average of, transmitted intensity in each band, which is then passed to the intensity data item register 34 for storage.

A calculation means 35 evaluates the data at points along the line scan of the bottle and attempts to fit it to a relationship in accordance with the method of the invention.

To carry out a bottle scan test to analyse the bottle contents a bottle to be investigated is loaded into the bottle holder. The x-ray beam is started and the bottle is moved to a position for scanning for example to a position that maximises the thickness of the contents through which the x-ray beam passes.

The embodiment of the method requires an $I_0$ reference dataset for the source across the spectrum under test which is conveniently generated in a calibration step before scanning by operating the system without an object.

In the preferred embodiment, a library of data is then generated of intensity information for contained liquids of known composition in known containers by scanning and determining attenuation of a range of known liquid/containers. The database provides reference information for a full range of likely liquid/container combinations, thereby providing an accurate and rapid matching process for target liquids. In this way, a scanned container can be matched against the database of characteristics and a target liquid indentified. A method of populating such a library is described in more detail below.

An object under test comprising an unknown contained liquid may then be scanned. For example, in a possible methodology, a first moving scan is performed where an $I_0$ value is taken as constant during the scan and anomalies are identified by anomalous trend data in transmitted intensity I.

The moving scan identifies target sites for a second, static scan on which a more comprehensive analysis is performed with a view to materials identification. For example at least attenuation at each band ($I/I_0$) is calculated In a possible further approach, the calculation means also evaluates a ratio between successive intensity data items (for example, where data items are collected I1 to I5 relating to energy bands $c1$ to $c5$, the calculation means evaluates the quotient I1/I2, I2/I3, I3/I4, I4/I5). This calculation of such a quotient is capable in principle of removing from consideration variables, such as density and thickness, which do not vary with incident radiation energy, and therefore of providing a numerical indicator which is functionally related to energy, and consequently indicative of the primary energy-dependent variable, the mass attenuation coefficient, by fitting to a relationship as above described.

Figure 4:
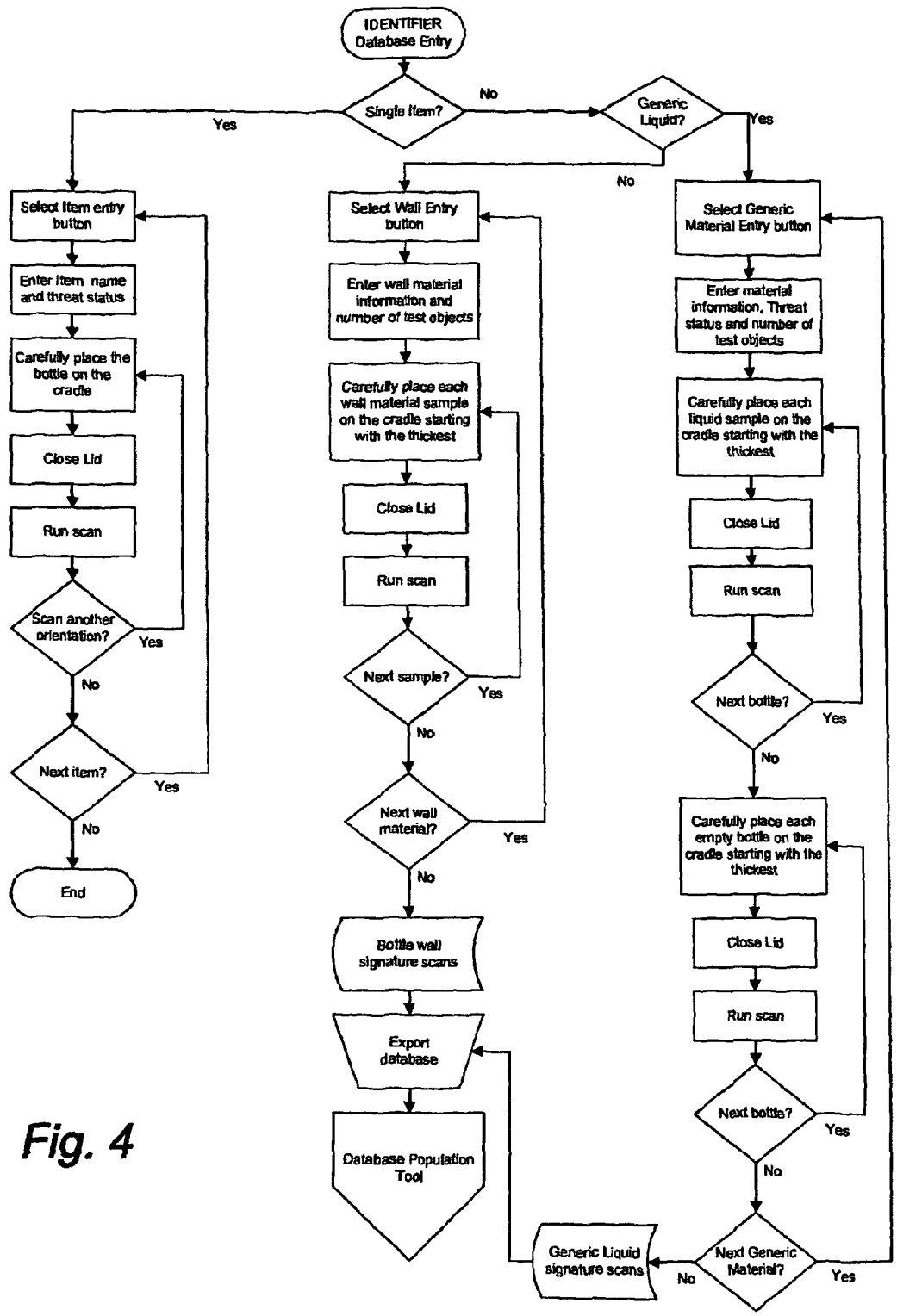
FIGS. 4 and 5 illustrates a representative protocol for top level data collection on the bottle scanner for production of a library of data in which data may be corrected for bottle tilt relative to the incident beam.
Figure 5:
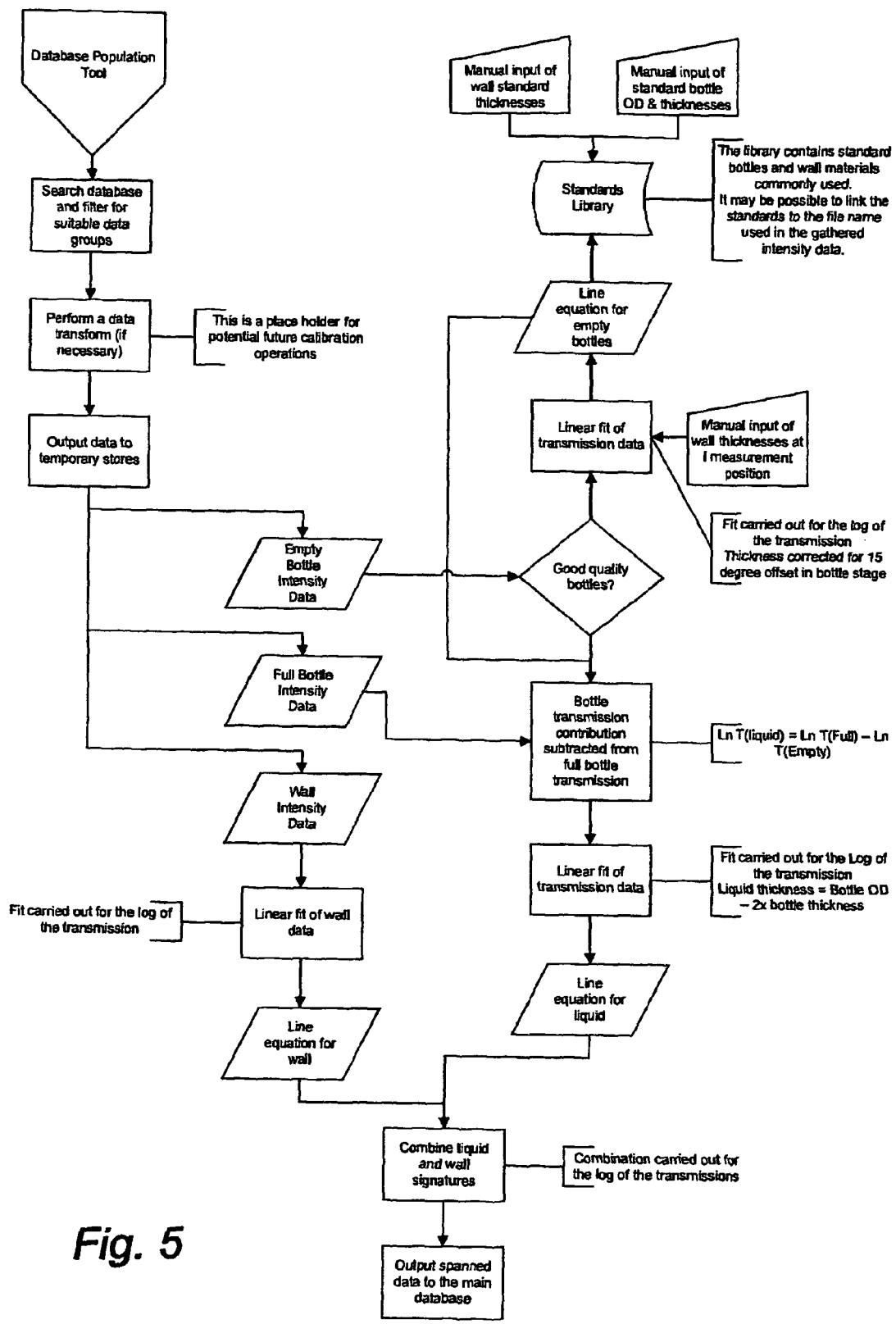

A comparator 36 compares the data thereby produced through the depth of the bottle with a library of data 37. The library of data includes pre-stored data of similar or at least numerically comparable nature which is related to or depends upon the expected attenuation of transmitted intensity, for example including the mass attenuation constant for a range of materials, and in particular specified target materials. The library of data includes intensity information for contained liquids of known composition in known containers across the spectrum of the radiation source for multiple permutations of different path lengths. This may be a manually or automatically addressed library. Data may be preloaded, or may be generated or added to over time by operation of the apparatus with known materials. FIG. 4, which continues into FIG. 5, is a representative protocol for top level data collection on the bottle scanner for production of such a library of data in accordance with the general principles of the invention. FIG. 5 illustrates the continuation of the protocol for bottle scanning depicted in FIG. 4, wherein the data may be corrected for bottle tilt relative to the incident beam.

By virtue of this comparison, inferences may be drawn about the likely material content in the transmission path. This may be displayed on the display means 38 or the display can preferably be delayed until the scan cycle is completed as described below.

In a possible embodiment a bottle is scanned in a stationary position. Such a static scan can be carried out at one selected point or, alternatively, a series of points for the static scan can be selected and a series of data records taken and analysed to identify or verify the material identity.

A series of static scans can be carried out if, for example, the contents of the bottle appear to have a layered composition or there appears to be a plurality of regions with different compositions.

The static scan position or positions can be determined by an automated system in association with the comparator or determined by an operator monitoring the test.

One position for the static scan might be selected in the neck of the bottle above the liquid level to get a background absorption of the x-ray beam for the material of the bottle.

The invention claimed is:

1. A method of obtaining radiation data useful for the identification and detection of composition of a contained material comprising the steps of:
  a) providing a radiation source and a radiation detector system spaced therefrom to define a scanning zone therebetween; the detector system being capable of detecting and collecting spectroscopically resolvable information about incident radiation;
  b) collecting intensity information about radiation incident at the detector system, and hence interaction of a container of known material composition and of known wall thickness, absent any contents, in the scanning zone with incident radiation from radiation received at the detector system after transmission through the container;
  c) repeating step b) for a plurality of different containers, each of known material composition and known wall thickness, and being absent any contents; to obtain a data set of intensity information relating to containers of known material compositions and known path length through the container;
  d) evaluating a numerical relationship relating to the plurality of containers to generate a first analytical function which describes spectroscopically resolvable intensity information about radiation incident at the detector system after interaction with a container of known material composition relative to the path length through the container;
  e) repeating steps b) to c) with the same containers now containing a contained material of known composition to obtain a data set of intensity information relating to container and contents of known material compositions and known path length through the container and contents;
  f) deconvolving the data generated at step e) from equivalent data generated for an empty container to obtain a data set of intensity information relating to contained material of known material composition to known path length through the contained material; and
  g) evaluating a numerical relationship relating to the data generated at step (f) to generate a second analytical function which describes spectroscopically resolvable intensity information about radiation incident at the detector system after interaction with a contained material of known composition relative to the path length through the contained material.

2. A method in accordance with claim 1 wherein steps b) to d) are repeated for a plurality of containers having different wall thicknesses and different material compositions.

3. A method in accordance with claim 1 wherein steps e) to g) are repeated for a plurality of contents having different compositions.

4. A method in accordance with claim 1 wherein data generated at step e) is used in the steps of:
  a) evaluating a numerical relationship relating to the plurality of containers containing contained materials of known material composition to generate a third analytical function which describes spectroscopically resolvable intensity information about radiation incident at the detector system after interaction with a container of known material composition and known thickness normal to the surface of the material of the container, containing a contained material of known composition; and
  b) subtracting the first analytical function from the third analytical function to provide the second analytical function.

5. A method in accordance with claim 1 wherein at least the first and second analytical functions are so developed as to describe intensity information about radiation incident at the detector system across the spectrum of the radiation source for multiple permutations of different path lengths.

6. A method in accordance with claim 1 wherein an analytical function relating intensity information about radiation incident at the detector system after interaction with a container and an analytical function relating to deconvolved intensity information about radiation incident at the detector system after interaction with a contained material are combined to produce an output which describes intensity information about radiation incident at the detector system after interaction with a contained material of known composition as it passes through the scanning zone across the spectrum of the radiation source for multiple permutations of different path lengths.

7. A method in accordance with claim 6 wherein the container analytical function and the contained material analytical function may be combined to populate a database with a range of virtual filled bottles of multiple permutations of different radiation path lengths.

8. A method in accordance with claim 1 wherein a step of collecting intensity information about radiation incident at the detector system after interaction with a container and/ or its contents comprises at least detecting radiation transmitted through the container and/ or its contents.

9. A method in accordance with claim 8 comprising the specific step of determining the attenuation of incident radiation by a container and/ or its contents in the scanning zone during a scanning step.

10. A method in accordance with claim 1 wherein incident intensity is measured via a calibration step in which the system is operated without an object in the scanning zone and intensity information about radiation incident at the detector system is used to generate an incident intensity dataset.

11. A method in accordance with claim 1 wherein an object to be scanned is a contained material in a bottle and the bottle is mounted in a holder and moved through a plane at an angle of between 5° and 30° from the vertical.

12. A method in accordance with claim 1 wherein an object to be scanned is oriented relative to the radiation beam such that the radiation beam is arranged to pass through the object at an angle of between 0° and 30° away from normal to the surface.

13. A method in accordance with claim 1 wherein the radiation source comprises a source to deliver high-energy ionising radiation.

14. A method in accordance with claim 1 wherein the radiation source beam is collimated to produce a pencil beam.

15. A method in accordance with claim 1 wherein the radiation beam is collimated after interaction with a container and/ or its contents under test to allow transmitted radiation to pass to the detector but to restrict any scatter radiation from reaching the detector.

16. A method in accordance with claim 1 wherein the detector system exhibits a spectroscopically variable response across at least a part of the source spectrum and the method comprises retrieving intensity information spectroscopically resolved at a plurality of differentiated energy bands across the spectrum of the source.

17. A method in accordance with claim 16 wherein the detector comprises a detector element fabricated from a semiconductor material or materials selected to exhibit inherently as a direct material property a direct variable photoelectric response to source radiation.

18. A method in accordance with claim 17 wherein the detector comprises a semiconductor material or materials formed as bulk single crystal including a Group II-VI semiconductor material.

19. A method in accordance with claim 17 wherein the detector comprises a semiconductor material selected from cadmium telluride, cadmium zinc telluride (CZT), cadmium manganese telluride (CMT) and alloys thereof.

20. A method in accordance with claim 1 wherein the contained material is a liquid.

21. A method for the identification and detection of composition of a contained material comprising the steps of:
  performance of the steps in accordance with claim 1 to generate the said analytical functions, and to generate a library of data of intensity information for contained materials of known composition in known containers;
  collecting intensity information about radiation incident at the detector system, and hence interaction of, an unidentified contained material, from radiation received at the detector system after transmission through the unidentified contained material; and
  comparing measured intensity data for the unidentified contained material with the said library of data of intensity information to identify the contained material.

22. A method of obtaining radiation data useful for the identification and detection of composition of a contained material comprising the steps of:
  a) providing a radiation source and a radiation detector system spaced therefrom to define a scanning zone therebetween; the detector system being capable of detecting and collecting spectroscopically resolvable information about incident radiation;
  b) collecting intensity information about radiation incident at the detector system, and hence interaction of a container of known material composition and of known wall thickness, absent any contents, in the scanning zone with incident radiation from radiation received at the detector system after transmission through the container;
  c) repeating step b) for a plurality of different containers, each of known material composition and known wall thickness, and being absent any contents; to obtain a first data set of intensity information relating to containers of known material compositions and known path length through the container;
  d) formulating a first analytical function using the first data set which describes spectroscopically resolvable intensity information about radiation incident at the detector system after interaction with a container of known material composition relative to the path length through the container, the first analytical function capable of providing spectroscopically resolvable intensity information about radiation incident at the detector system after interaction with containers in addition to containers for which intensity information is provided in the first data set;
  e) repeating steps b) to c) with the same containers now containing a contained material of known composition to obtain a second data set of intensity information relating to container and contents of known material compositions and known path length through the container and contents;
  f) either (i) subtracting measured empty container data from measured filled container data; or (ii) using the first analytical function to generate empty container data virtually and subtracting the virtual empty container data from the measured filled container data to obtain a third data set of intensity information relating to contained material of known material composition to known path length through the contained material; and
  g) formulating a second analytical function using the third data set which describes spectroscopically resolvable intensity information about radiation incident at the detector system after interaction with a contained material of known composition relative to the path length through the contained material, the second analytical function capable of providing such intensity information for contained material in addition to contained material for which intensity information is provided in the third data set.

23. A computer programmed method of generating a database of radiation data useful for the identification and detection of composition of a contained material, the computer programmed to execute the following steps:
  a) retrieving a plurality of sets of intensity information about radiation incident at a detector system, the detector system being capable of detecting and collecting spectroscopically resolvable information about incident radiation received from a radiation source, each set of intensity information representing interaction of a container of known material composition and of known wall thickness, absent any contents, in a scanning zone between the radiation source and the detection system, with incident radiation from radiation received at the detector system after transmission through the container;
  b) generating a first data set from the plurality of sets of intensity information relating to containers of known material compositions and known path length through the container;
  c) generating a first analytical function using the first data set which describes spectroscopically resolvable intensity information about radiation incident at the detector system after interaction with a container of known material composition relative to the path length through the container, the first analytical function capable of providing spectroscopically resolvable intensity information about radiation incident at the detector system after interaction with containers in addition to containers for which intensity information is provided in the first data set;
  d) retrieving a plurality of sets of intensity information about radiation incident at a detector system, each set of intensity information representing interaction of one of the containers of known material composition and known wall thickness, containing a contained material of known composition and generating a second data set of intensity information relating to container and contents of known material compositions and known path length through the container and contents;
  e) either (i) subtracting the retrieved empty container data of the first data set from the retrieved filled container data of the section set; or (ii) using the first analytical function to generate virtual empty container data and subtracting the virtual empty container data from the retrieved filled container data to obtain a third data set of intensity information relating to contained material of known material composition to known path length through the contained material; and f) formulating a second analytical function using the third data set which describes spectroscopically resolvable intensity information about radiation incident at the detector system after interaction with a contained material of known composition relative to the path length through the contained material, the second analytical function capable of providing such intensity information for contained material in addition to contained material for which intensity information is provided in the third data set.

24. A method of obtaining radiation data useful for the identification and detection of composition of a contained material comprising the steps of:

a) providing a radiation source and a radiation detector system spaced therefrom to define a scanning zone therebetween; the detector system being capable of detecting and collecting spectroscopically resolvable information about incident radiation;

b) collecting intensity information about radiation incident at the detector system, and hence interaction of a container of known material composition and of known wall thickness, absent any contents, in the scanning zone with incident radiation from radiation received at the detector system after transmission through the container;

c) repeating step b) for a plurality of different containers, each of known material composition and known wall thickness, and being absent any contents; to obtain a data set of intensity information relating to containers of known material compositions and known path length through the container;

d) evaluating a numerical relationship relating to the plurality of containers to generate a first analytical function which describes spectroscopically resolvable intensity information about radiation incident at the detector system after interaction with a container of known material composition relative to the path length through the container;

e) repeating steps b) to c) with the same containers now containing a contained material of known composition to obtain a data set of intensity information relating to container and contents of known material compositions and known path length through the container and contents;

f) evaluating a numerical relationship relating to the plurality of containers containing contained materials of known material composition to generate a third analytical function which describes spectroscopically resolvable intensity information about radiation incident at the detector system after interaction with a container of known material composition and known thickness normal to the surface of the material of the container, containing a contained material of known composition; and g) subtracting the first analytical function from the third analytical function to provide the second analytical function.

* * * * *